US009414842B2

(12) United States Patent
Glimsdale et al.

(10) Patent No.: US 9,414,842 B2
(45) Date of Patent: Aug. 16, 2016

(54) MULTI-COMPONENT VASCULAR DEVICE

(75) Inventors: Matt C. Glimsdale, St. Michael, MN (US); Paul A. Pignato, Stacy, MN (US); Matt C. Heidner, Maple Grove, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 1798 days.

(21) Appl. No.: 11/974,398

(22) Filed: Oct. 12, 2007

(65) Prior Publication Data

US 2009/0099647 A1   Apr. 16, 2009

(51) Int. Cl.
*A61B 17/08* (2006.01)
*A61B 17/12* (2006.01)
*A61B 17/00* (2006.01)

(52) U.S. Cl.
CPC ....... *A61B 17/12022* (2013.01); *A61B 17/0057* (2013.01); *A61B 17/12036* (2013.01); *A61B 17/12109* (2013.01); *A61B 17/12113* (2013.01); *A61B 17/12122* (2013.01); *A61B 17/12172* (2013.01); *A61B 2017/00473* (2013.01); *A61B 2017/00526* (2013.01); *A61B 2017/00575* (2013.01); *A61B 2017/00867* (2013.01); *A61B 2017/12054* (2013.01); *A61B 2017/12095* (2013.01)

(58) Field of Classification Search
CPC ............. A61B 17/0057; A61B 17/12036; A61B 17/12113; A61B 17/12172; A61B 17/12022; A61B 17/12109; A61B 17/12122; A61B 2017/12095; A61B 2017/00526; A61B 2017/00867; A61B 2017/00473; A61B 2017/00575; A61B 2017/12054

USPC .......... 606/200, 213, 151; 128/831; 623/1.16
See application file for complete search history.

(56) References Cited

U.S. PATENT DOCUMENTS

| 5,725,552 | A | 3/1998 | Amplatz et al. | |
|---|---|---|---|---|
| 5,827,285 | A * | 10/1998 | Bramlet | 606/60 |
| 5,846,261 | A | 12/1998 | Amplatz et al. | |
| 5,944,738 | A | 8/1999 | Amplatz et al. | |
| 6,123,715 | A | 9/2000 | Amplatz | |
| 6,368,339 | B1 | 4/2002 | Amplatz | |
| 6,447,531 | B1 | 9/2002 | Amplatz | |
| 6,468,303 | B1 | 10/2002 | Amplatz et al. | |
| 6,506,204 | B2 | 1/2003 | Mazzocchi | |
| 6,579,303 | B2 | 6/2003 | Amplatz | |

(Continued)

OTHER PUBLICATIONS

Definition on the term "tubular" based on dictionary.com, http://dictionary.reference.com/browse/tubular.*

(Continued)

*Primary Examiner* — Jing Ou
(74) *Attorney, Agent, or Firm* — Armstrong Teasdale LLP

(57) ABSTRACT

A vascular occlusion, flow restriction, shunt or filter device is disclosed comprising the assembly of at least two, of a number of selectable discrete interconnectable, interchangeable components, at least one component being of the type fabricated from metal strands braided into a tubular metal fabric having an expanded preset configuration and an elongated, collapsed reduced diameter configuration for delivery through a catheter to a treatment site and the device shaped to create an occlusion, flow restriction or shunt when placed in an opening in a body organ or vessel, the woven metal fabric having a memory property whereby the medical device tends to return to said expanded preset configuration when unconstrained.

19 Claims, 20 Drawing Sheets

(56) References Cited

U.S. PATENT DOCUMENTS

| | | |
|---|---|---|
| 6,599,308 B2 | 7/2003 | Amplatz |
| 6,638,257 B2 | 10/2003 | Amplatz et al. |
| 6,663,607 B2 | 12/2003 | Slaikeu et al. |
| 6,682,546 B2 | 1/2004 | Amplatz |
| 7,001,409 B2 | 2/2006 | Amplatz |
| 2003/0055455 A1* | 3/2003 | Yang et al. ............ 606/215 |
| 2003/0100920 A1* | 5/2003 | Akin et al. ............ 606/213 |
| 2003/0149463 A1* | 8/2003 | Solymar et al. .......... 623/1.1 |
| 2003/0187495 A1 | 10/2003 | Cully et al. |
| 2004/0167597 A1 | 8/2004 | Costantino et al. |
| 2005/0222488 A1 | 10/2005 | Chang et al. |
| 2005/0228434 A1 | 10/2005 | Amplatz et al. |
| 2006/0106418 A1* | 5/2006 | Seibold et al. .......... 606/213 |
| 2006/0241687 A1* | 10/2006 | Glaser et al. ........... 606/213 |
| 2006/0241690 A1 | 10/2006 | Amplatz et al. |
| 2006/0247680 A1 | 11/2006 | Amplatz et al. |
| 2006/0259127 A1 | 11/2006 | Tolomeo et al. |
| 2007/0106328 A1* | 5/2007 | Wardle et al. ........... 606/213 |
| 2007/0179527 A1* | 8/2007 | Eskuri et al. ........... 606/213 |
| 2007/0233186 A1* | 10/2007 | Meng ................... 606/213 |
| 2007/0265656 A1 | 11/2007 | Amplatz et al. |
| 2007/0265658 A1* | 11/2007 | Nelson et al. ........... 606/213 |
| 2007/0293889 A1* | 12/2007 | Corcoran et al. ......... 606/213 |
| 2007/0293891 A1* | 12/2007 | Corcoran et al. ......... 606/213 |
| 2008/0065148 A1* | 3/2008 | Corcoran et al. ......... 606/213 |
| 2008/0281350 A1* | 11/2008 | Sepetka et al. .......... 606/200 |

OTHER PUBLICATIONS

Definition on the term "tube" based on dictionary.com, http://dictionary.reference.com/browse/tube.*

* cited by examiner

MULTI-COMPONENT VASCULAR DEVICE

BACKGROUND OF THE INVENTION

I. Field of the Invention

The present invention generally relates to collapsible therapeutic intravascular devices for treating certain medical conditions and, more particularly, relates to intravascular devices selectively configured of discrete components for selective occlusion of a vessel or vessel defect, shunting of flow, restricting flow or filtering flow in a vessel or organ, anywhere within the body's circulatory system. The devices made in accordance with the invention are particularly well suited for delivery through a catheter or the like to a remote location in a patient's vascular system within a patient's body to occlude, shunt, restrict or filter blood flow.

II. Related Art

A wide variety of intravascular devices are used in various medical procedures. Certain intravascular devices, such as balloon catheters, diagnostic catheters, stent delivery catheters and guidewires, are generally used simply to navigate, deliver fluids or other medical devices to specific locations within a patient's body, such as a selective site within the vascular system. Other, frequently more complex, devices are used in treating specific conditions, such as devices used in removing vascular occlusions or for treating septal defects and the like.

In certain circumstances, it may be necessary to occlude a patient's vessel, chamber, channel, hole or cavity such as to stop blood flow there through. In other cases, it may be necessary to create a flow restriction or to shunt flow from one vessel to another to treat abnormal cardiovascular conditions. In still other cases, it may be desirable to filter blood flow such as to prevent blood clots or emboli from passing from one location in a vessel to another.

Examples of selective occlusion are, without limitation, closure of a Patent Ductus Arteriosus (PDA), Atrial Septal Defect (ASD), Ventricular Septal Defect (VSD), Patent Foreman Ovale (PFO), Arterial Venous Fistula (AVF), an Arterial Venous Malformation (AVM) or a Left Atrial Appendage (LAA).

Mechanical embolization devices are well known in the art and sold commercially for occlusion of vessels in various locations within the vasculature. U.S. Pat. No. 6,123,715 by Amplatz and U.S. Pat. No. 5,725,552 by Kotula disclose intravascular occlusion devices fabricated from Nitinol braided metal tubular fabric which are heat set in molds to an expanded shape, but which can be compressed for delivery through a catheter to a treatment site, whereby the device, when urged out of the delivery catheter, self expands within the vasculature to occlude blood flow at the treatment site. The details of the various designs and configurations as well as methods of fabricating and using the devices are detailed in the aforementioned patents which are deemed incorporated in total herein by reference for any purpose.

An example of a shunting procedure is the shunting of blood between the portal vein and the hepatic vein, know as a Transjugular Intrahepatic Portosystemic Shunt (TIPS). Certain forms of congenital disease may require a communication between the right atrium and left atrium. Shunting may also be required for treating specific abnormal conditions, such as bi-passing vascular occlusions within an internal passageway. U.S. Pat. No. 6,468,303 to Amplatz et al, also incorporated in its entirety herein by reference for any purpose, describes catheter deliverable shunt devices manufactured in similar fashion to the previously discussed occlusion devices and also details their design and use.

Many defects that involve holes or openings in the septum of the heart allow blood to flow from the high pressure left ventricle to the lower pressure right ventricle causing excess blood flow to the lungs. The body's natural reaction is to constrict the vessels to the lungs to restrict blood flow. Over time this causes a thickening of the pulmonary arteries and ultimately to closure of smaller lung arteries and further complications if left untreated. Examples of flow restriction devices for treating such a condition, their design and use, are found in U.S. Pat. No. 6,638,257 to Amplatz which is also deemed incorporated in its entirety herein by reference for any purpose.

An example of a filtering procedure is a vena cava filter used to prevent passage of blood clots from the venous system to the lungs. Another filtering procedure involves prevention of emboli from balloon or stenting procedures from passage down stream into the heart while treating saphenous vein bypass grafts or preventing emboli from passing to the brain during carotid artery stenting procedures. An example of a filtering device for treating such a condition, it's design and use is found in U.S. Pat. No. 6,123,715 to Amplatz and U.S. Pat. No. 5,725,552 to Kotula as previously cited and incorporated by reference.

The occluding, shunting and flow restricting devices all use similar technology for fabrication and each device as detailed is formed of a single plurality of metal strands woven into a tubular braid. Due to the wide anatomical range of dimensions between premature infants and adult patients, variations between patients of even the same body size, and considering the number of various treatment modalities, one can appreciate the enormous number of sizes and types of devices that need to be manufactured and inventoried by both the manufacturer and the hospital. This represents a large amount of capital sitting on the shelf until the need arises for a particular type and size of device. To reduce inventory, would require that devices be ordered in advance as needed. This presents a problem for emergency cases when there is afforded no time for waiting to treat a patient while a device is manufactured or shipped from stock if available.

Therefore there is a need for medical devices of the class that can be assembled by either the manufacturer or preferably by the physician at the point of use from an array of component parts that meets the needs of physicians without undue delay or inventory cost. Furthermore, there is a need for a physician to be able to assemble a large number of custom devices suitable for a particular anatomical condition from a variety of components available in a medical device kit, or the like, made available at the point of use instead of stocking a large number of various types and sizes of assembled devices.

The present advance in the art solves these problems in an advantageous manner as will be explained in this specification.

SUMMARY OF THE INVENTION

By means of the present invention, collapsible therapeutic medical devices are supplied by assembly from a plurality of selected discrete parts, which devices are well suited for the selective occlusion, filtering, shunting, or flow restriction of a vessel, lumen, channel, cavity, or organ accessible from anywhere within the body's circulatory system.

The present invention provides a variety of vascular occlusion, filter, flow restriction, or shunt devices that can be easily fabricated by the assembly of at least two of a number of selectable individual interconnectable components. Preferably, as needed for delivery, at least one component is of a collapsible type fabricated at least in part from braided tubular metal fabric having a preset expanded configuration when unconstrained and an elongated reduced diameter collapsed configuration to enable delivery of a device using a vascular catheter to a treatment site. Such components are shaped to create an occlusion, filter, flow restriction or shunt device when placed in an opening in a body organ or vessel, the woven metal fabric exhibiting a memory property whereby a medical device component fabricated using such material tends to return to an expanded preset configuration when unconstrained.

Each of the components available for assembly into the device is provided with a connection element on at least one end and preferably on both ends to allow for inter-connectivity between or among a plurality of components and to a delivery element or system. Each component is either dimensioned to be passed through a delivery catheter or is collapsible by elongation to enable passage through a delivery catheter.

A wide variety of component shapes and sizes are contemplated to allow assembly of devices to fit particular anatomical and treatment needs of particular patients. Each of a large number of sizes and types of available parts or components are contemplated to be individually packaged for selective assembly into a full device at the time of use in a procedure. Preferably, components will be supplied in sterilized pouches or trays although the components may also be sterilized by other means even at the hospital site.

In one embodiment of the device of the invention, the connections are threaded and a given device is fabricated by threading one selected component onto mating threads on another selected component. The proximal end of the assembled medical device is threaded onto a delivery element used to advance the device through a delivery catheter introduced into the vasculature and placed adjacent the treatment site. The delivery system (also referred to as the delivery device or element) allows the assembled medical device to be passed out the distal end of a catheter lumen whereby the assembled medical device is enabled to return to its preset expanded configuration. The assembled medical device of a preferred embodiment is further configured so that it remains attached to the delivery system until detached by an operator and may be pulled back into the catheter by the delivery element, if needed, for example, to reposition the medical device or the medical device may be withdrawn back out of the body if it or a component of it is not of the correct size. When the intravascular medical device is placed as desired, the delivery element is unthreaded from it and removed along with the delivery catheter from the body.

In accordance with the present concept, in the event that a device being deployed has one or more components found not to be the correct size, selected components may be readily replaced by different sized components obviating the need to change out the entire device. This can be accomplished by unthreading the component and replacing it by threading on a different selected new component. This enables one to customize aspects of the device by replacement of only necessary components thereby enabling a cost saving over replacement of a complete device.

One aspect of the invention is the provision of medical devices assembled from selected multiple discrete interconnectable components, particularly those for treating vascular or organ abnormalities which necessitate occlusion, filtering, flow restriction or shunting as the means of treatment.

Another aspect of the invention is the provision of a method of assembly of medical devices using selected multiple components that may either be assembled by the manufacturer or assembled by the physician at the point of use generally within the catheter lab of a hospital. When the medical devices are assembled by the manufacturer in this manner, savings occur by reductions of inventory to components that can be readily assembled to meet a wide variety of customer custom medical device needs. This reduces lead time between the order and shipment of devices and simplifies the manufacturing process. When the device is assembled by a physician from pre-sterilized components that are stocked in the hospital or readily available from a sales person or distributor, the needs of any particular patient can be met when time is of the essence such as in an emergency.

In addition, the physician is able to assemble a custom device to meet the particular anatomical needs of a patient that may be sufficiently unusual so as to preclude the availability of a required assembled medical device as a standard product offering. As previously mentioned, the perceived patient vessel or cavity size may be different in actuality from that determined by ultrasound or angiographic means. If a device was ordered for a particular patient and, in the middle of the procedure, the device is found not to fit, presently, the physician has no option but to cancel the procedure and reschedule when the correct device is available or the physician would have had to order several devices of various sizes to reduce the risk of a misfit. This is costly and unused devices increase inventory cost. On the other hand by use of the inventive in situ assembly of the device the physician can change a component of the system for another component during a procedure and continue the case to a successful conclusion.

In another aspect, the invention involves a method of treating medical conditions necessitating the occlusion, filtering, flow restriction, or shunting of a vessel or organ within the body, by use of a medical device comprising multiple discrete interchangeable components that are selectively interconnectable, either at the manufacturer or at the point of use within a hospital catheter lab.

Many of the devices designed as occlusion devices have configurations that include flange or disk shapes at one end or spaced flange or disk shapes at both ends. Flange or disk shapes may be combined with other shapes adjacent to the flange or disk such as cylinders, tapered cylinders, etc. A spacer may be provided between two end disks or flanges that may have any number of shapes. The spacer may be coiled or looped or be elastic to allow the overall device to accommodate variations in the length of the path to be occluded. In many cases (but not all) the spacer may be fabricated from a braided tubular fabric that has a heat set memoried expanded state and a reduced diameter elongated shape for passage through a catheter. It may be fabricated from Nitinol wire, or any of a variety of other memoried materials as will be discussed. In some cases there is no spacer and the device takes on a shape more like a bell with a flange or disk end and an adjacent short cylinder tapered at the distal end as shown in the above-referenced patents. Flow restrictor and shunt devices may also have shapes that have flange or disk-like members at one or more ends. Filters may have funnel or disk-like members as well.

In accordance with another aspect of the present invention, common shaped elements of a variety of current medical devices can be fabricated as discrete components with connectors at one or both ends that mate with compatible connectors on other components such that a single medical device can be fabricated by consecutive assembly in a longitudinal manner of a plurality of components end to end along a common axis.

Another advantage of the concept is that each component of a device may be fabricated using different materials and processes. In a one piece device all aspects of the device must be fabricated from the same braided fabric. This may present limitations in the shape that can be obtained or limit the characteristics of the device. In a multi-component device each component may be fabricated to have a particular set of characteristics that would not be obtainable from a single braided fabric. For example, one component may have different flexibility, elongation radial expansion force as by altering the number of wires, wire diameter, material of the wires, or the pitch of the braid. In a filter, one component may be specifically fabricated for anchoring properties while another component may be fabricated for filtering particular sized emboli.

These and other features and advantages of the inventive design will become readily apparent to those skilled in the art from a review of the drawings and the detailed description in conjunction with the accompanying claims.

BRIEF DESCRIPTION OF THE DRAWINGS

Generally, FIGS. 1-26 represent prior art devices, but also represent designs that could be fabricated using the multi-component device invention disclosed herein. FIGS. 27-39 represent various components that may be used to assemble devices using the invention.

FIG. 1 is a side view of a round double disk occluder having concave surfaces on each disk, the concave surfaces being generally parallel;

FIG. 2 is a side view of a round double disk occluder having a cylindrical central portion and concave surfaces on each disk in opposed or mirror image relation;

FIG. 3 is a side view of a round double disk occluder similar to FIG. 2 but with reduced distance between the disks and a recess in one disk to accommodate a securement means;

FIG. 4 is a side view of a round double disk occluder having one large disk with a concave surface and a relatively smaller disk spaced tightly within the confines of the large disk;

FIG. 5 is a side view of a round double disk occluder having outward facing concave disks and a large diameter long central cylindrical section between the disks, each of which has recesses for the securement means;

FIG. 6 is a side view of a round double disk occluder having a large disk with a deep concave surface facing a smaller disk having a deep concave surface and a loop connector between the disks;

FIG. 7 is a side view of a round double disk occluder having two different diameter disks with shallow concave surfaces facing each other and a small diameter long cylindrical section between the disks;

FIG. 8 is a side view of a double disk occluder similar to that of FIG. 6 except that the disks have shallower concave surfaces and a coil connector is provided between the disks;

FIGS. 9 and 10 are side and top views respectively of a shunt device having an eccentric lumen and two disks with recessed securement connectors;

FIG. 11 is a side view of a round occluder having a single flange and a tapered diameter portion adjacent with recessed surfaces to accommodate the securement element;

FIGS. 12 and 13 are side views of round occluders having a disk at one end, recessed surfaces at each end for the securement means or element, a rounded flange at the opposite end and a large diameter, long cylindrical central portion with the disk of FIG. 12 located eccentric to the central portion;

FIGS. 15 and 16 are side and top views of a bell shaped PDA (Patient Ductus Arteriosus) occluder having a single fabric layer construction;

FIGS. 17 and 18 are top and side views of a flanged occluder;

FIGS. 19 and 20 are side and top views respectively of an occluder similar to that of FIG. 1 but fabricated with multiple layers of fabric;

FIGS. 21 and 22 are side and top views, respectively, of an occluder similar to that of FIGS. 15 and 16 but fabricated of multiple layers of fabric;

FIG. 23 is a perspective view of a collapsible medical device for use as a flow restrictor shown in its expanded state;

FIG. 24 is a side view of the occluder of FIG. 7 occluding a passageway in the body;

FIG. 25 is a side view, with parts cut away, of an occluder shown occluding an aneurysm;

FIG. 26 is a sectional view of the heart showing a PDA (Patent Ductus Arteriosus) occluder in use;

FIG. 29 is a side view of a discrete cylindrical component having recessed areas on both end surfaces for securement connectors;

FIG. 30 shows a side view of a discrete component for a PDA occluder;

FIG. 31 shows a side view of a discrete component of an occluder for a vessel or cavity;

FIG. 32 shows a side view of a discrete component of a flanged occluder;

FIG. 36 is a cross-sectional view of a ball & socket connector with articulation;

DETAILED DESCRIPTION

Figure 1:
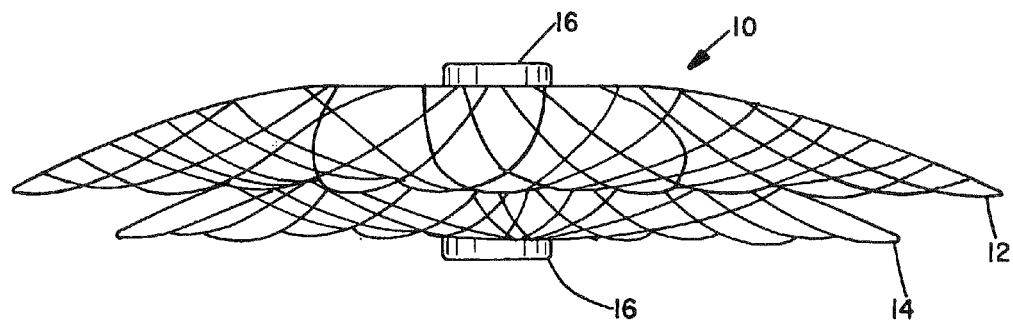

The present invention provides vascular occlusion, filtering, flow restriction, or shunt devices made up of the assembly of at least two, of a number of selectable individual components, at least one component being of the type fabricated from metal strands braided into a tubular metal fabric (described below) having an expanded preset configuration and an elongated, collapsed reduced diameter configuration for delivery through a vascular catheter to a treatment site wherein the device is shaped to create an occlusion, flow restriction or shunt when placed in an opening in a body organ or vessel, the woven metal fabric having a memory property whereby the medical device tends to return to an expanded preset configuration when unconstrained.

The metal strands define two sets of essentially parallel generally helical strands, with the strands of one set having a "hand", i.e. a direction of rotation, opposite that of the other set. This defines a generally tubular fabric, known in the fabric industry as a tubular braid. The Amplatz and Kotula patents previously discussed describe tubular fabric medical devices and the methods of fabrication of such devices in great detail and further detailed discussion is believed not needed here.

The pitch of the wire strands (i.e. the angle defined between the turns of the wire and the axis of the braid) and the pick of the fabric (i.e. the number of wire crossovers per unit length) may be adjusted as desired for a particular application. The wire strands of the metal fabric used in the present method should be formed of a material which is both resilient and which can be heat treated to substantially set a desired shape. Materials which are suitable for this purpose include a cobalt-based low thermal expansion alloy referred to in the field as Elgeloy, nickel-based high temperature high-strength "super-alloys" commercially available from Haynes International under the trade name Hastelloy, nickel-based heat treatable alloys sold under the name Incoloy by International Nickel, and a number of different grades of stainless steel. An important factor in choosing a suitable material for the wires is that the wires retain a suitable amount of the deformation induced by a molding surface (as described below) when subjected to a predetermined heat treatment.

One class of materials which also meet these qualifications includes so-called shape memory alloys such as Nitinol, an approximately stoichiometric alloy of nickel and titanium, which may also include minor amounts of other metals to achieve desired properties. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing. These alloys are also very elastic and have been described as "superelastic" or "pseudoelastic".

As an example, without limitation, the device can be illustrated being fabricated from 32 braided nitinol wires having a diameter ranging from 0.0015-0.008 inch (0.0381-0.203 mm), preferably 0.002-0.005 inch (0.051-0.127 mm). The number of wires to be braided may range from 4-200 or more, preferably from 8 to 144 and, more preferably, from 16-72 depending on the particular device characteristics desired. A typical pitch angle may range from 30-70 degrees from the longitudinal axis of the braided tube in the, as braided, relaxed tube prior to heat treatment. As indicated, the pitch, pick count (number of wire crossovers per inch, or other lineal measure) and wire diameter, are all variables that can be altered to change the device characteristics as well as the heat set shape.

In forming a medical device component in accordance with the invention, an appropriately sized piece of the metal fabric is cut from the larger piece of fabric which is formed, for example, by braiding wire strands to form a long tubular braid, as has been described. When the fabric is cut to the desired dimensions, care should be taken to ensure that the fabric will not unravel.

Thus, the ends at the selected desired length may be soldered, brazed, welded or otherwise affixed together (e.g. with a biocompatible cementitious organic material) before the braid is cut.

Once an appropriately sized piece of the metal fabric is obtained, the fabric is deformed to generally conform to a surface of a molding element. The forming of the fabric re-orients the relative positions of the strands of the metal fabric from their initial order to a second, re-oriented configuration. The shape of the molding element should be selected to deform the fabric into substantially the shape of the desired component of the medical device.

Once the molding element is assembled with the metal fabric generally conforming to a molding surface of that element, the fabric can be subjected to a heat treatment while it remains in conforming contact with that molding surface. After the heat treatment and cooling, the fabric may be removed from the molding element and it will substantially retain its deformed molded state. Suitable heat treatments of Nitinol wire, for example, to set a desired shape are well known in the art. It has been found that holding a Nitinol fabric in the range of about 500° C. to about 550° C. for a period of about 1 to about 30 minutes, depending on the softness or harness of the device to be made, will tend to set the fabric in its deformed state, i.e. wherein it conforms to the shape of the molding surface of the molding element. At lower temperatures, the required heat treatment time will tend to be greater (e.g. about one hour at about 350° C.) and at higher temperatures the time will tend to be shorter (e.g. about 30 seconds at about 900° C.).

Figure 34A:
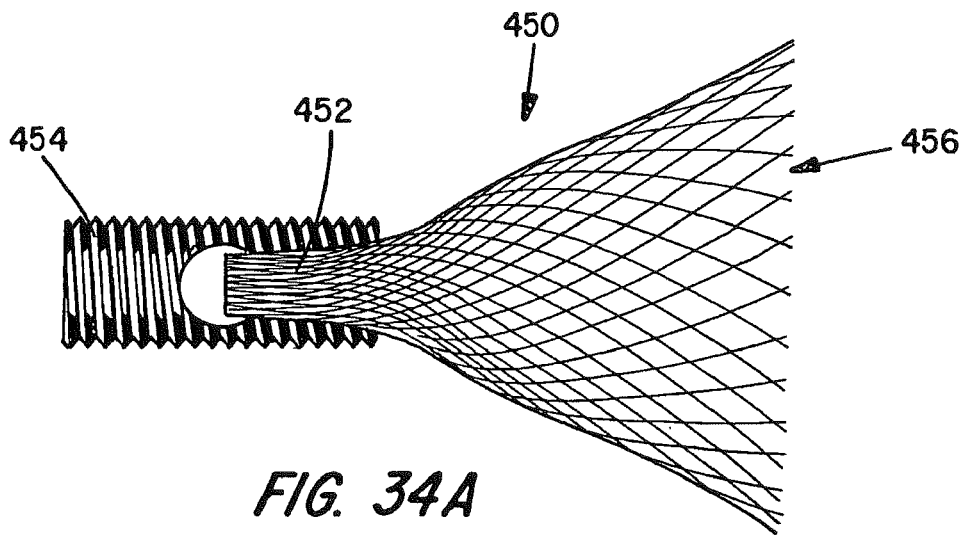
FIGS. 34A-B depict side and end views of a filter device component for use in a body channel.
Figure 34B:
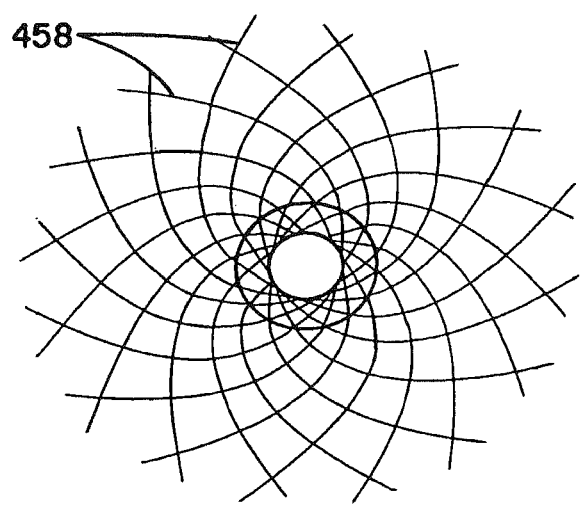

The ends of the braided metal fabric device component are generally welded or clamped together with clamp securements to avoid fraying. Of course the ends may alternately be held together by other means readily known to those skilled in the art. Alternatively, one end may be fabricated without the clamp as in the case of a conical filter, such as is shown in FIGS. 34A and 34B, since the heat set shape will resist unraveling of the strands.

As used herein, the terms securement, securement means, securement device, etc., refer to any device or technique including welding or use of adhesives, etc., to secure the ends of the braided metal fabric. Connector clamp, clamp connector, retaining connector, securement connector, etc., may be used interchangeably to refer to any devices or technique designed to retain the ends of the braided metal fabric and provide a connection with an adjacent component. The securement at an end, which ties together the wire strands, may also serve to connect the device component to other device components or to a delivery system. In a preferred embodiment, end clamps or securements are provided that are also part of the connectors and are generally cylindrical in shape and have a recess for receiving the ends of the metal fabric in a manner that substantially prevents the wires comprising the woven fabric from moving relative to one another. The securement connectors also are generally provided with a threaded surface. Either external (male) or internal (female), threads may be provided or, alternatively, any of a number of other connecting techniques known in the art may be employed to reversibly attach one component to an adjacent component in a multi-component device or to a delivery system. An ability for reversal or disassembly, while not mandatory, preferably should also be facilitated.

FIGS. 1-26 generally depict examples of some devices that can be fabricated using the inventive concept for the assembly of at least two components, such as those illustrated in FIGS. 27-33.

More particularly, FIGS. 1-8 illustrate a variety of designs that may be described as having axially aligned flanged or disk elements, one at each end, with a connective member positioned between them. The shape and size of the connective members may vary widely from very thin loop or coil sections to heavy cylindrical sections and from very short to very long sections. The devices of FIGS. 9-26 generally could be described as devices having a flange or disk at one end only with an adjacent connecting shape attached thereto.

FIG. 1 is a side view of a round double disk occluder 10 having concave surfaces on each disk 12 and 14 with the concave surfaces being generally parallel. A cylindrical central portion is shown at 16.

Figure 2:
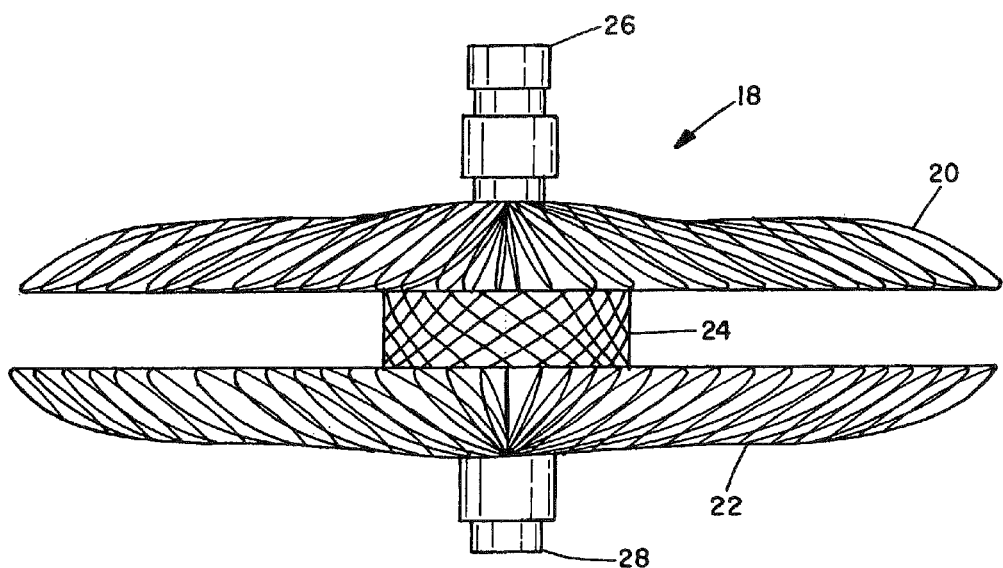
Figure 3:
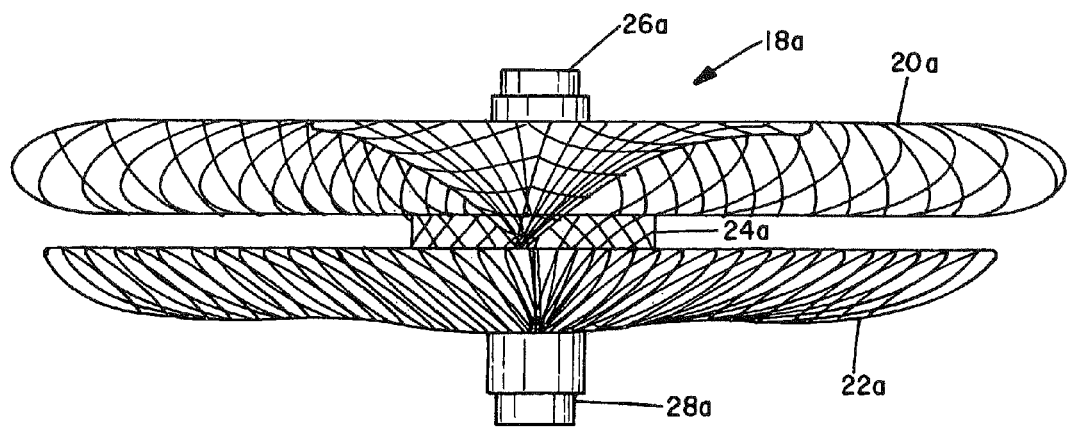
Figure 4:
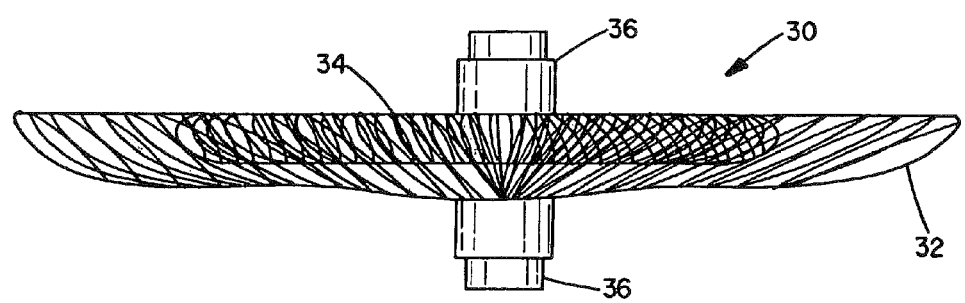

FIGS. 2 and 3 show similarly shaped round double disk occluders 18 and 18a, respectively. The disks 20, 22 and 20a and 22a have opposed concave inner surfaces. These devices have cylindrical central portions as at 24 and 24a, respectively, with the central portion 24 being longer than the central portion 24a. External securement connectors are shown at 26, 28 and 26a and 28a, respectively. FIG. 4 depicts a side view of a round double disk occluder 30 having one large disk 32, with a concave surface and an opposing smaller disk 34 that is spaced tightly within the confines of the large disk. External securement connectors are provided as at 36.

Figure 5:
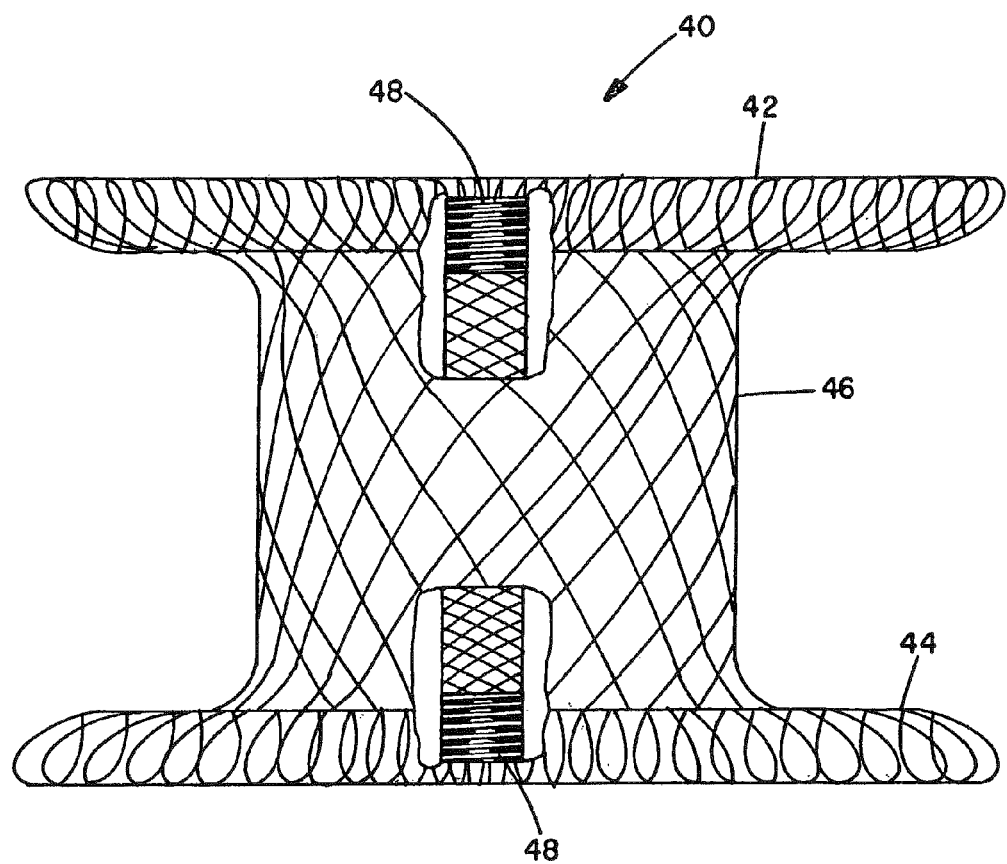

FIG. 5 is a side view of a round double disk occluder generally at 40 having spaced outward facing concave disks 42 and 44 and a large diameter long central cylindrical connecting section between the disks shown at 46. The disks are provided with recesses which incorporate securement connector elements as at 48.

Figure 6:
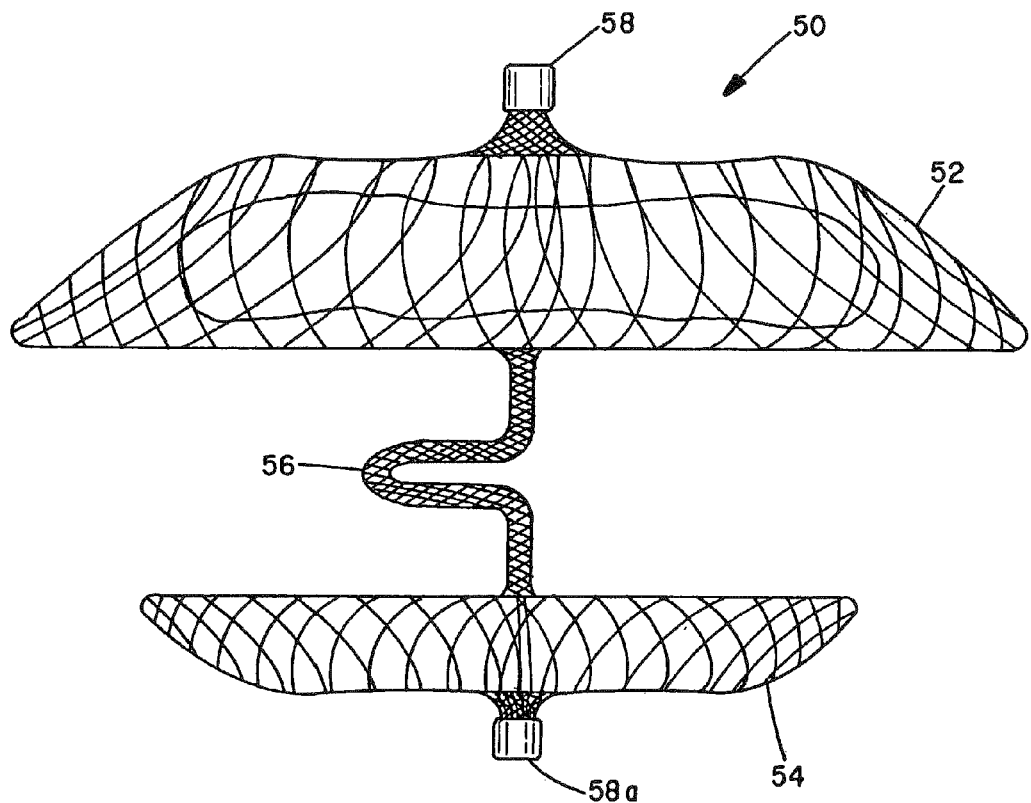
Figure 8:
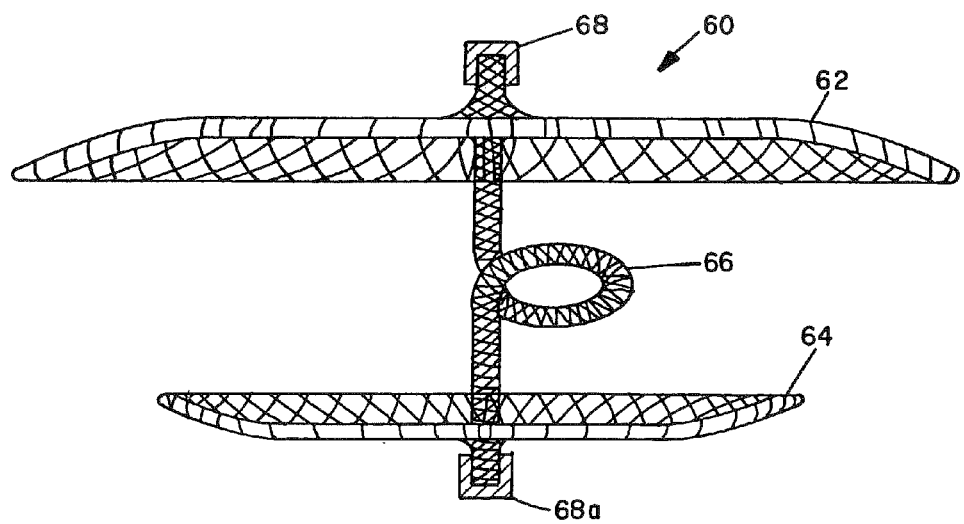

FIG. 6 is a side view of a round double disk occluder 50 including opposed disks. A large disk 52 with a deep concave surface faces a smaller disk 54, also having a deep concave surface. These are connected by a rather long loop connector 56. External securement connector devices are shown at 58. FIG. 8 is a side view of a double disk occluder 60 which is similar to that of FIG. 6 except that the disks 62 and 64 have shallower concave surfaces formed by a looped coil 66 is shown attached between the disks. External clamps or securement connectors are also shown at 68 and 68a.

Figure 7:
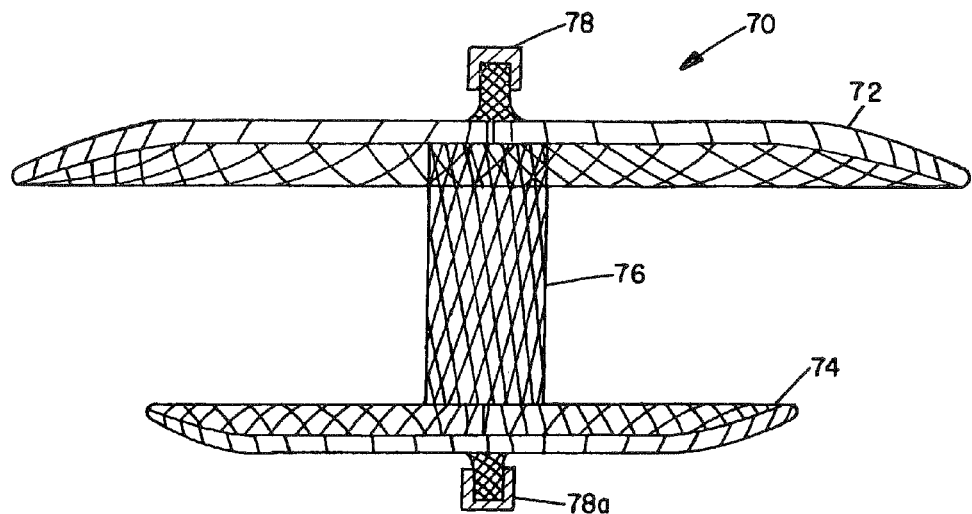
Figure 24:
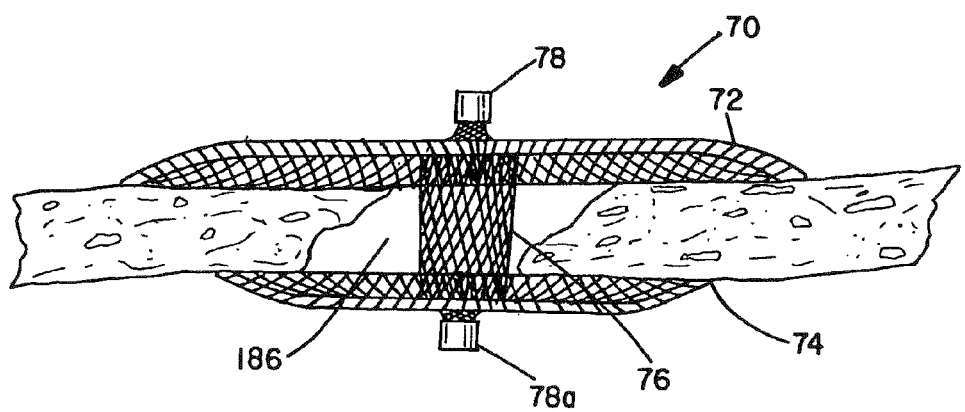

FIG. 7 is a side view of a round double disk occluder 70 having two disks 72 and 74 of different diameters featuring opposed shallow concave surfaces facing each other with a rather long cylindrical section 76 connecting the disks. External securement connectors are shown at 78 and 78a. FIG. 24 represents a view of the occluder 70 of FIG. 7 deployed to occlude a defect 186 in a vessel wall or membrane at 188.

Figure 9:
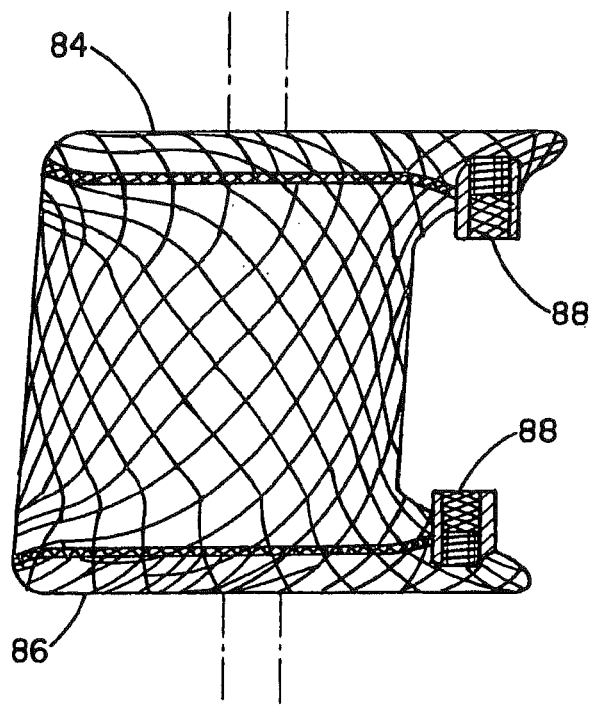
Figure 10:
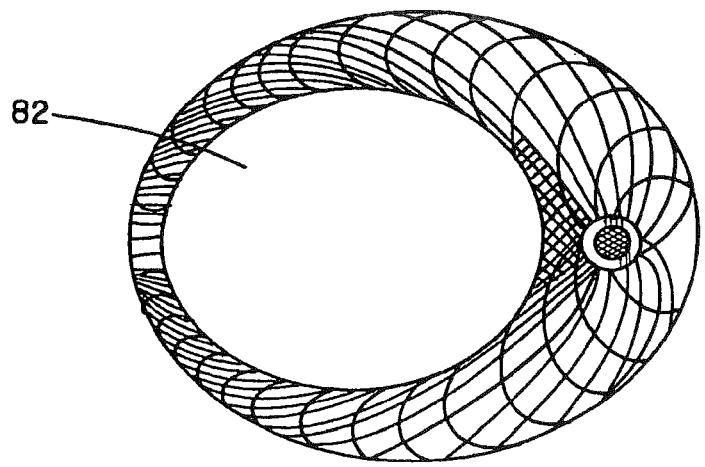

FIGS. 9 and 10 are side and top views, respectively, of a shunt device 80 connected by an eccentric large diameter cylinder having a lumen 82 and two disks 84 and 86 with recessed securement connectors 88.

Figure 11:
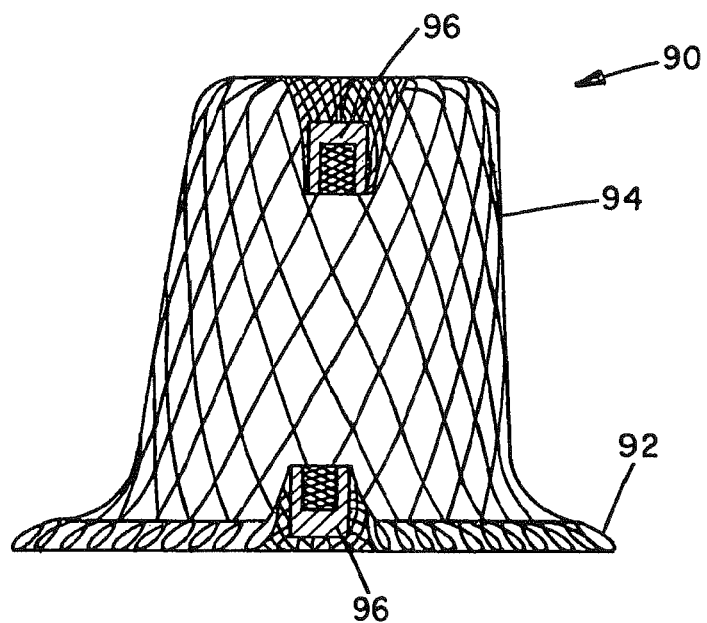
Figure 12:
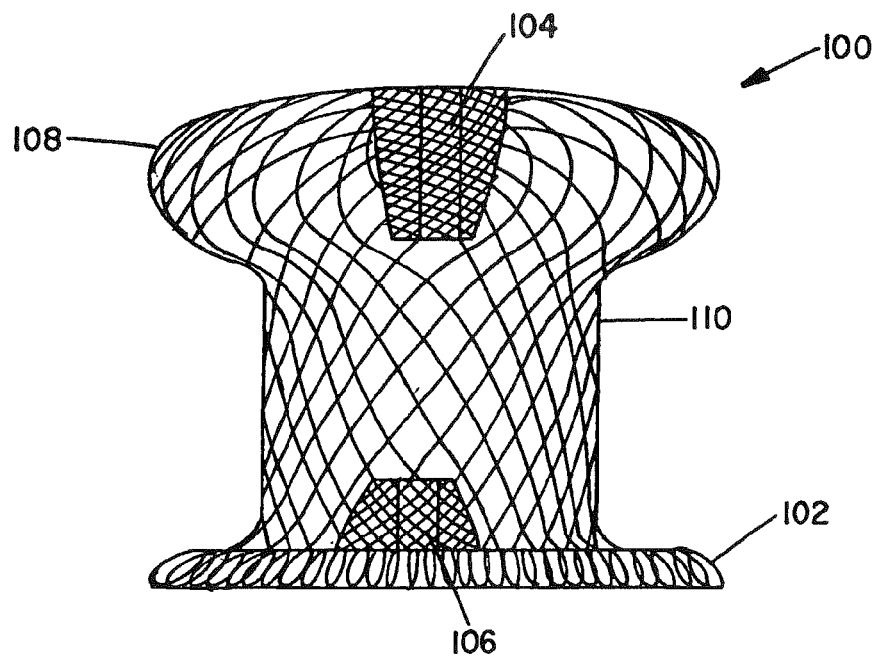
Figure 13:
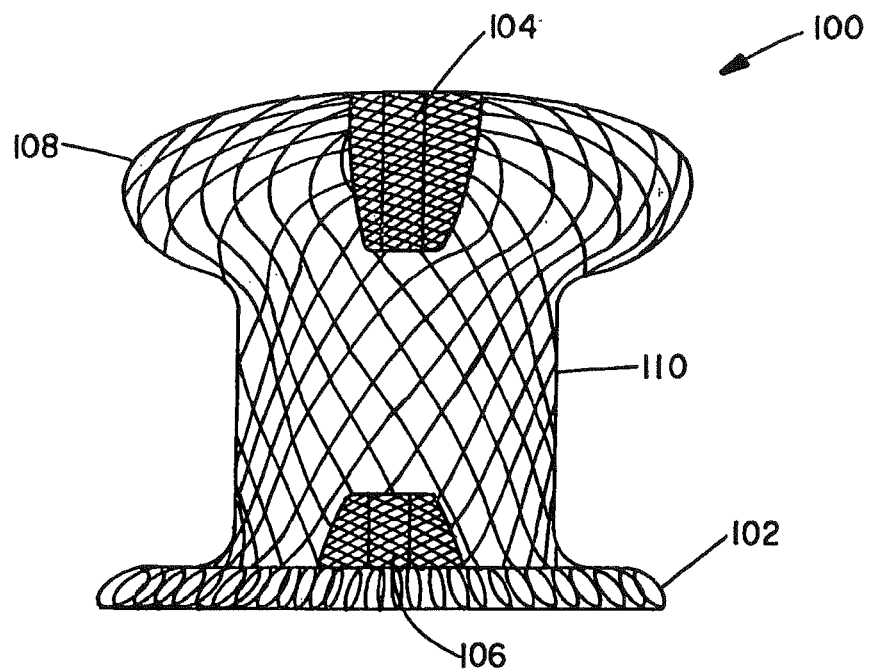

FIG. 11 is a side view of a round occluder 90 having a single flange 92 and a tapered diameter adjacent component portion 94 with recessed securement connectors 96. FIGS. 12 and 13 are side views of single flange similar round occluders 100 and 100a having a disk 102 at one end and recesses 104 and 106. The occluder 100 further includes a rounded flange 108 and a large diameter, long cylindrical central portion at 110. The disk 102 in FIG. 12 is eccentric to the central portion 110.

Figure 14A:
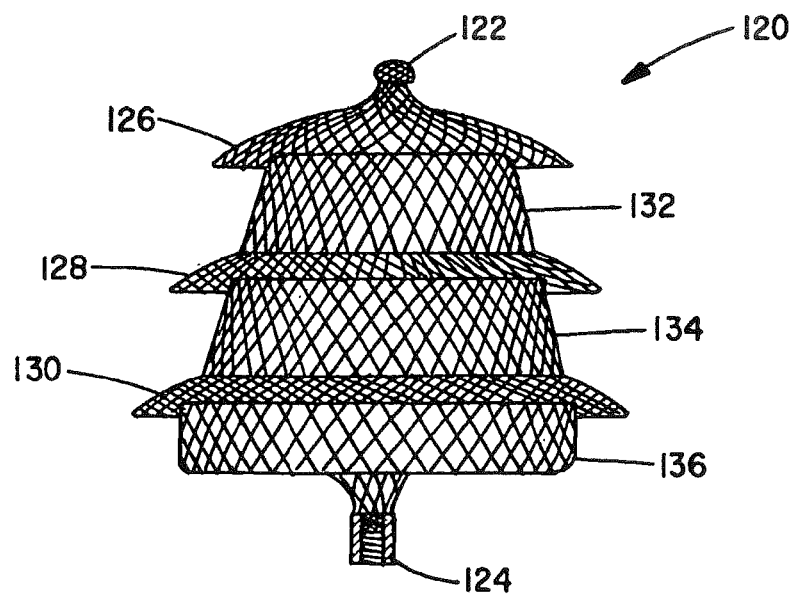
FIGS. 14A and 14B are side and installed use views, respectively, of a round flanged occluder with a tapered length.
Figure 14B:
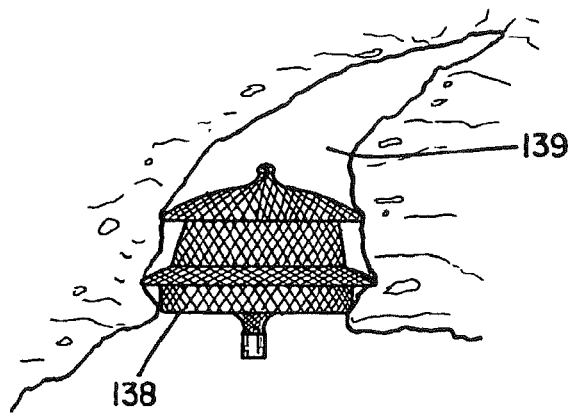

FIGS. 14A and 14B are side and installed views, respectively, of round, multi-flanged occluders with a tapered length. Securement connectors are shown at 122 and 124. That device contains consecutive, spaced conclave flanges of increasing sizes as shown at 126, 128 and 130. They are joined by conical internal sections 132 and 134. An outer cylindrical section is provided at 136. In FIG. 14B, a similar two-flanged device 138 is shown installed to occlude a defect at 139.

Figure 15:
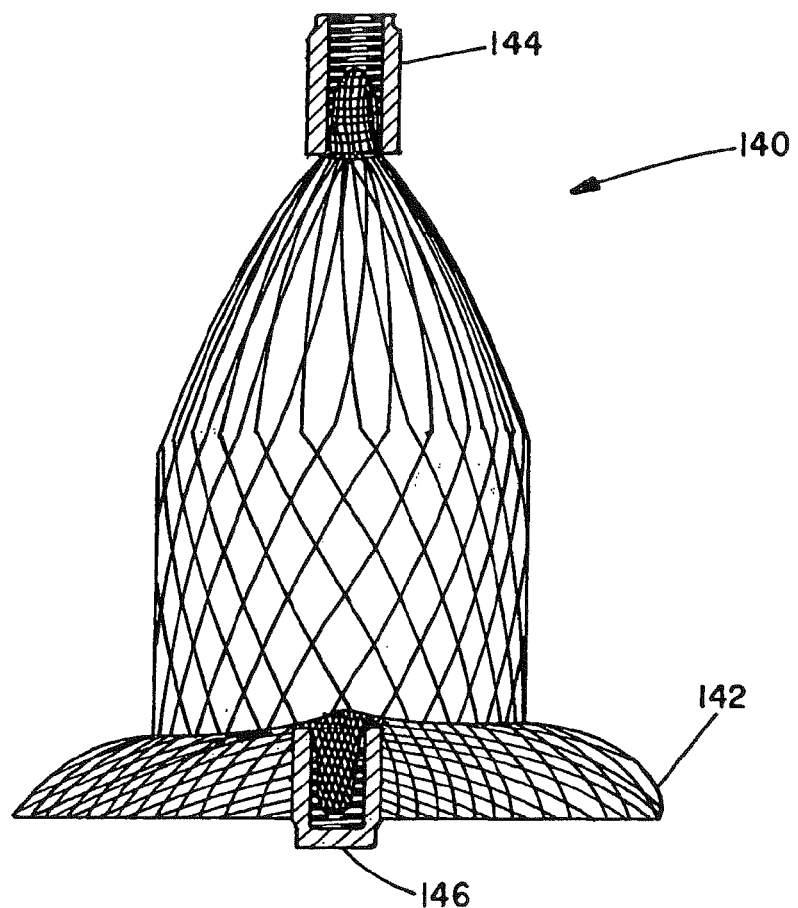
Figure 16:
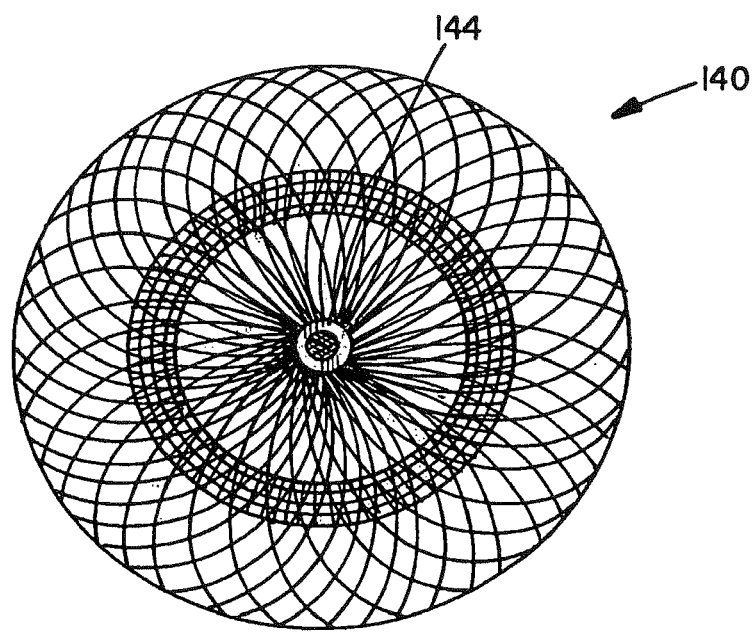
Figure 21:
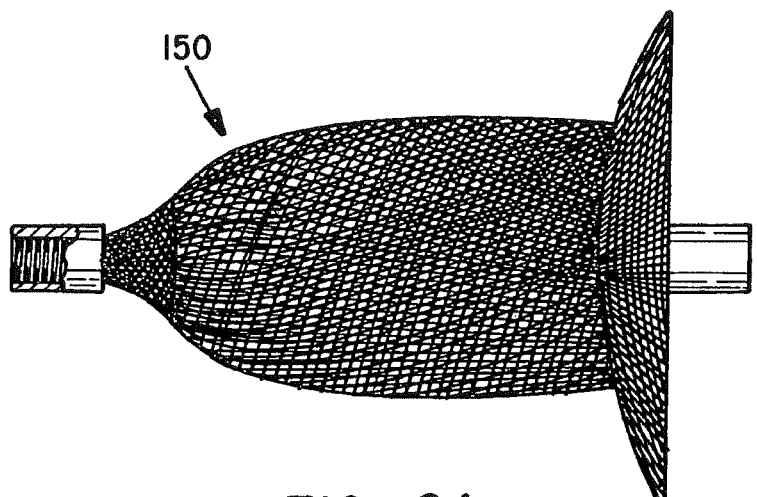
Figure 22:
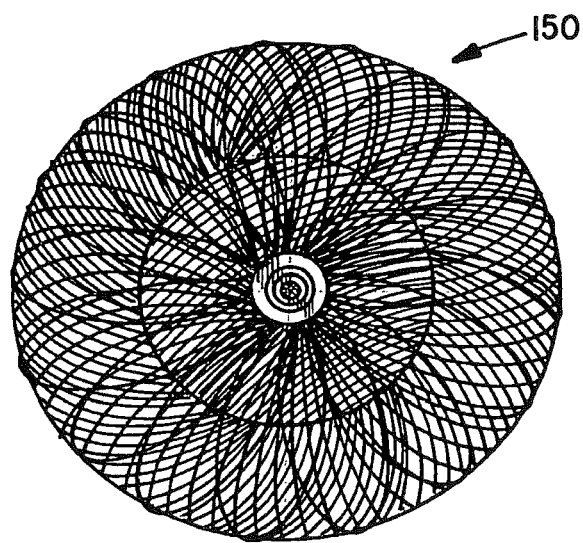
Figure 26:
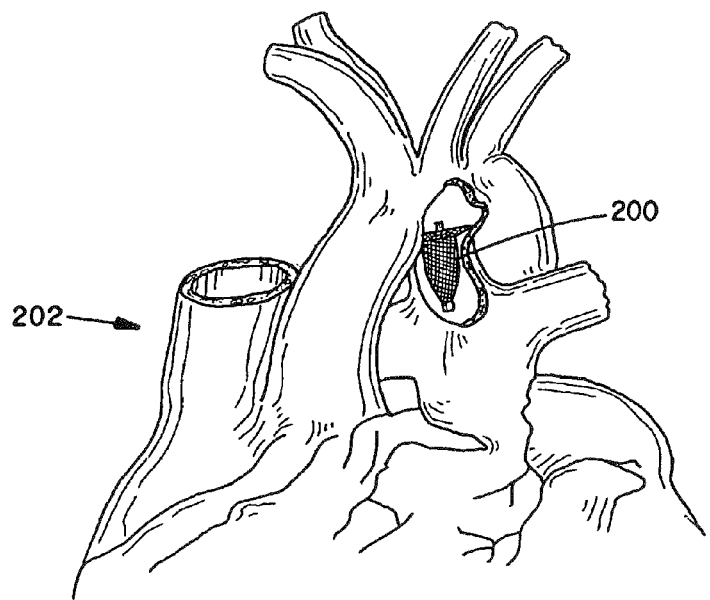

FIGS. 15 and 16 are side and top views, respectively, of a bell-shaped PDA occluder 140, which is fabricated using a single layer of fabric and includes a recessed flange 142 and securement and connecting devices at 144 and 146. FIGS. 21 and 22 are side and top views, respectively, of an occluder 150 similar to that shown in FIGS. 15 and 16, but fabricated using multiple layers of fabric. FIG. 26 is a sectional view of the heart showing a PDA occluder 200 in place in a heart 202.

Figure 17:
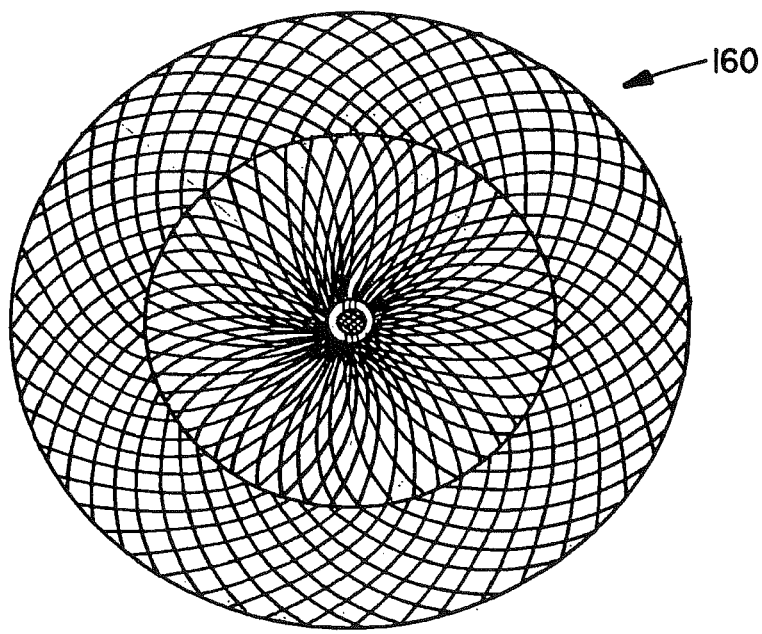
Figure 18:
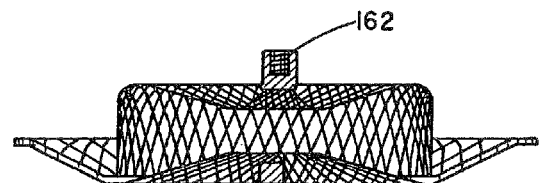
Figure 19:
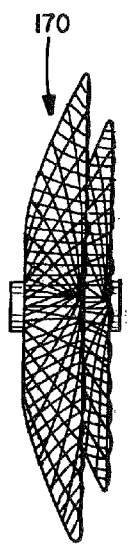
Figure 20:
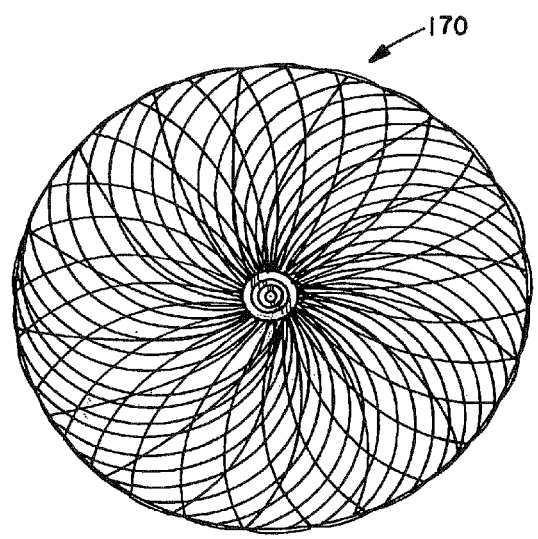

FIGS. 17 and 18 represent top and side views of a single flanged occluder 160 with side securement connectors at 162 and 164. FIGS. 19 and 20 are side and top views, respectively, of an occluder very similar to that shown in FIG. 1 fabricated with multiple layers of fabric.

Figure 23:
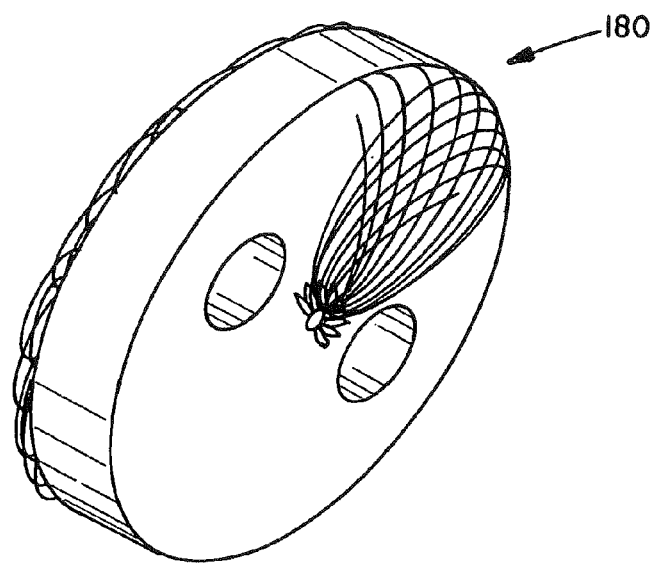

FIG. 23 depicts a perspective view of a collapsible flow restrictor device 180 in its expanded state.

Figure 25:
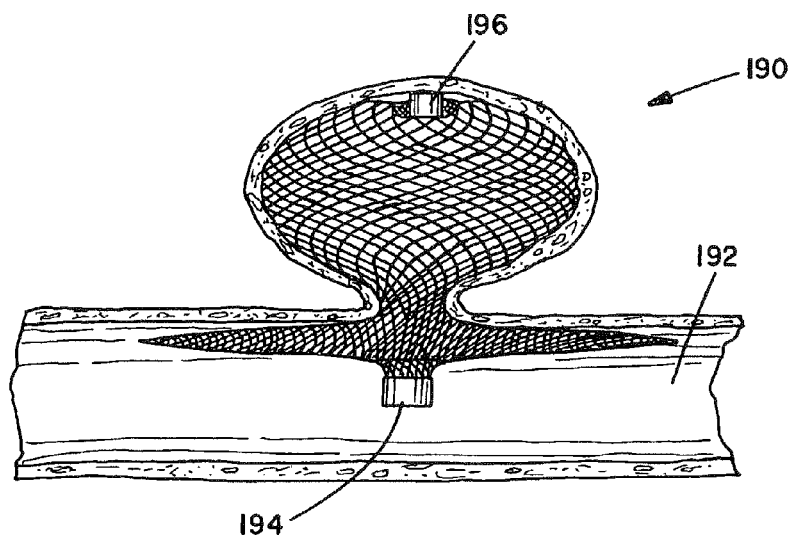

FIG. 25 is a side view, with parts cut away, of an occluder 190 occluding an aneurism in a vessel at 192. Securement connectors are shown at 194 and 196.

FIGS. 27A-I through FIG. 36 and FIGS. 39A-C illustrate examples of components likely to be assembled into multi-component devices such as those illustrated in FIGS. 1-26 according to the invention. FIGS. 27A-I are illustrations of example flange or disk-shaped components 300-315 selectable to be incorporated in a final device. Each of the flange or disk components illustrated in FIGS. 27A-I are provided with a pair of female threads in securement connectors at each end as at 316 and 318 of flange 300. Component 315, shown in section, is provided with a single female connector through the proximal side. While the clamp or securement extensions containing the female threads may be larger as at 320 in flange 308, the female threads as at 322 in flange 308 are preferably all of a uniform size to accommodate a variety of the connector devices having a common thread size. Examples of such devices are shown in FIGS. 28A-G as at 350, 352, 354, 356, 358, 360 and 361. These may range from loop-connectors as in FIG. 28C, rather large diameter straight or tapered cylinders as at 356 and 358, respectively. A round shape is shown at 360 in FIG. 28F and a spring component at 361. In this regard, however, as with the flange and disk parts of FIGS. 27A-I, male threaded connectors as at 362 and 364 of FIG. 28A are provided with a common size and threading and all of the devices of FIGS. 28A-F and which correspond to the female threads of FIGS. 27A-I.

Figure 30:
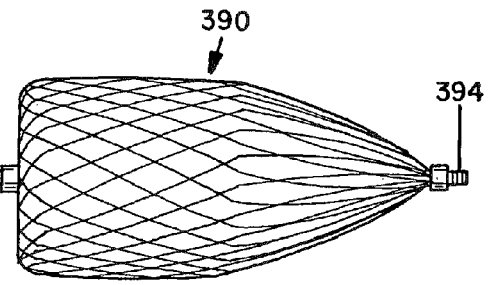

Other parts are shown in FIGS. 29-33. Thus, in FIG. 29 there is shown a side view of a discrete cylinder component 380 having recessed areas on both end surfaces for securement devices and being supplied with threaded securement connectors at 382 and 384. In FIG. 30, there is another view of a single layer discreet component for a PDA occluder at 390 and having male threaded connectors on both ends at 392 and 394.

Figure 31:
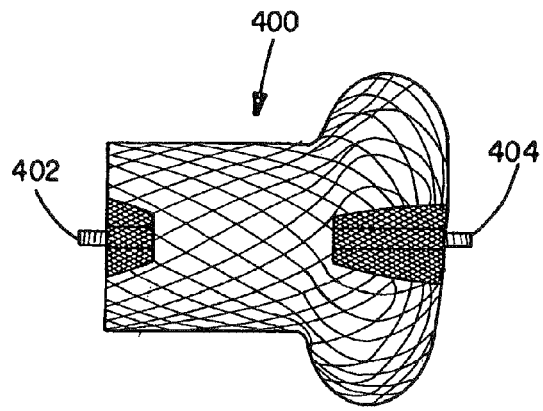
Figure 32:
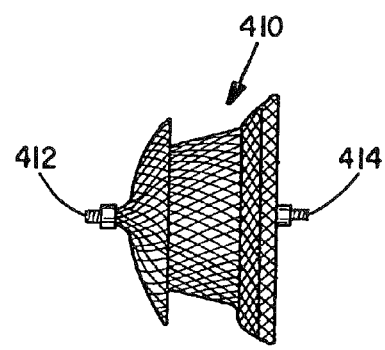

FIG. 31 depicts a component of a rounded occluder suitable for a vessel or cavity at 400 with male threaded securement connectors at 402 and 404. FIG. 32 depicts a double flange component of a flanged occluder at 410 with male threaded securement connectors shown at 412 and 414.

Figure 33A:
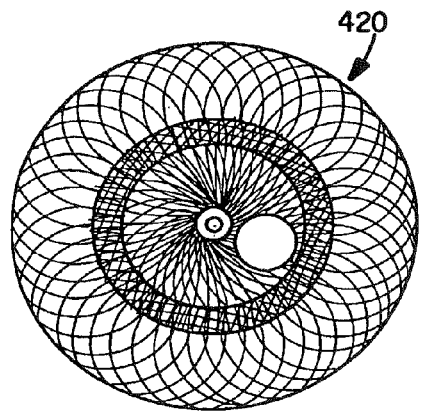
FIGS. 33A-B show a top/end view and a sectional view, respectively, of a discrete component of a flow restrictor or a shunt device.
Figure 33B:
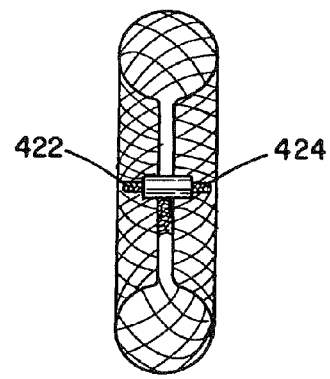

FIGS. 33A and 33B depict a top/end view and a sectional view, respectively, of a discreet component 420 of a flow restrictor or shunt device with recessed threaded securement connectors shown at 422 and 424.

FIGS. 34A and 34B depict an embodiment of a component suitable for use as a filter for a body cavity such as a blood vessel or other cavity. The filter 450 has a generally conical configuration tapering generally radially outward from a first and end 452 which is shown clamped in a threaded male connector 454 to a forward or second end 456 which is flared and sized to completely fill the channel to be filtered. Fabric ends 458 are shown unsecured.

Figure 38A:
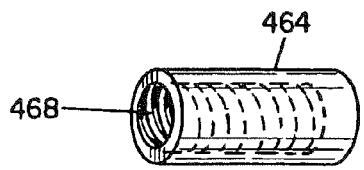
FIGS. 38A-C show parts for securement connector devices in accordance with the invention.
Figure 38B:
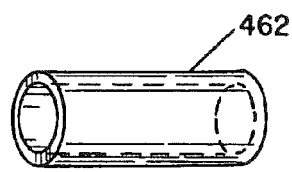
Figure 38C:
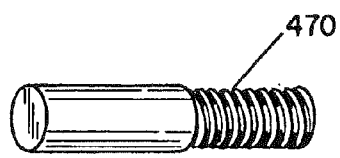

The views of 37A and 37B and 38A-C depict a typical securement connector device 460 which includes an outer tubular member or sleeve 462 and an inner tubular member or sleeve 464. The combination of the outer sleeve member or sleeve 462 and sleeve member 464 cooperated to clamp and secure fabric end fibers as at 466 therebetween. The sleeve member 464 is also provided with a female thread at 468 to connect to an adjacent interconnectable component or a delivery device or system. Alternatively, the inner member may be provided with a male thread connection as shown at 470 in FIG. 38C.

Figure 39A:
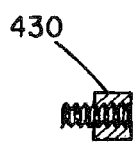
FIG. 39A-C are enlarged views of threaded adapters including a male/female thread adapter 34 (A) a male to male thread adapter 34 (B) and a female to female thread adapter 34 (C).
Figure 39B:
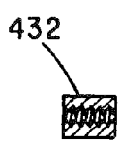
Figure 39C:
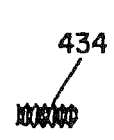

FIGS. 39A-C are slightly enlarged views of a male/female thread adaptor 430 in view 34A; a male to male thread adaptor 432 shown in view 34B; a female to female thread adaptor 434 shown in view 34C.

The clamp connectors that are attached to components as shown in FIGS. 27A-I and 34A and B, or the like, for example, are, as described above, fabricated using inner and outer sleeves. A female inner sleeve has a bore that is threaded with a given thread such as 000-120. A second outer sleeve has an inside diameter of sufficient size to accommodate the braid fabric end wires as well as the outside diameter of the inner sleeve. Once the wire ends are positioned between the two sleeves the assembly is laser welded together.

In the case of the end securement clamp connector attached to the middle or adjacent components as in FIGS. 28A-G, for example, the securement clamp connector is similarly fabricated from an inner and outer sleeve in a similar manner, except that the inner sleeve has a male thread that mates with the female thread of the securement clamp connectors of FIGS. 27A-H.

FIGS. 28A-G describe either middle or adjacent components designed to attach to those shown, for example, in FIGS. 27A-I and FIGS. 34A and B. The middle components are provided with male threads as extensions to their wire end securement clamps or other securement devices. These components readily assemble by threaded engagement to those of FIGS. 27A-I. To fabricate a device, for example, that shown in FIG. 7, one would thread component 350 of FIG. 28A into one end of component 300 of FIG. 27A, and the opposite end of component 350 to component 302 of FIG. 27B. Either end of the assembled device can then be threaded to a delivery system having a male thread on its distal end.

Of course, any of the components illustrated as having male threads could be provided with female threads and vise versa, or each device could have a male thread on one end and a female thread on the other end. The latter combination, however, is not the preferred embodiment as it is less flexible to assembly choices. In other embodiments, all components could be of either all male thread or all female threads. In this arrangement, it would be necessary to use thread adapter components as shown in FIGS. 39A-C. Since these components are small and may be difficult to handle, this construction is not the preferred embodiment, but is contemplated since it allows all devices to be fabricated with similar end wire clamp securement connectors. Still, this allows assembly of combination devices where otherwise a thread mismatch might occur with available parts, as during a procedure.

Notwithstanding the above, it will be appreciated that other means of preventing the fabric wire end from unraveling may be used such as crimping, use of adhesives, soldering, brazing etc. A suitable threaded connector is still advised in the preferred embodiments but is not required. One may use any other connection means suitable for the application as is known in the art. Alternatively, if the fabric is inverted at one end, the two wire ends may be brought together one atop the other and secured by a single clamp connector as illustrated in FIG. 27I. Additionally, the clamp may be removed from one end altogether with the wires heat set shape resisting unraveling though this is not a preferred configuration as illustrated in FIGS. 34A and B.

Figure 35A:
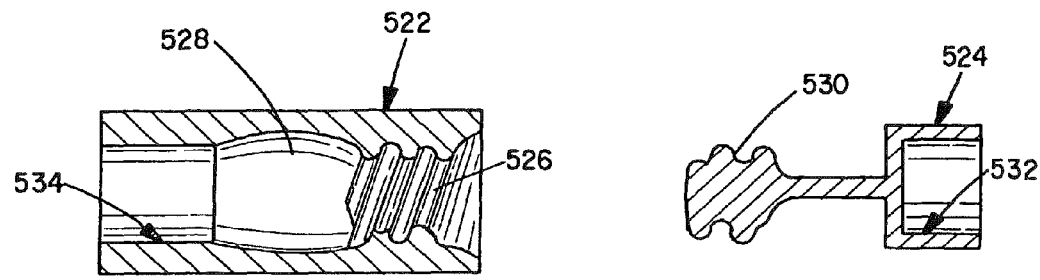
FIGS. 35A-B are cross-sectional views of a screw connector with articulation shown disassembled in FIG. 35A and assembled in FIG. 35B.
Figure 35B:
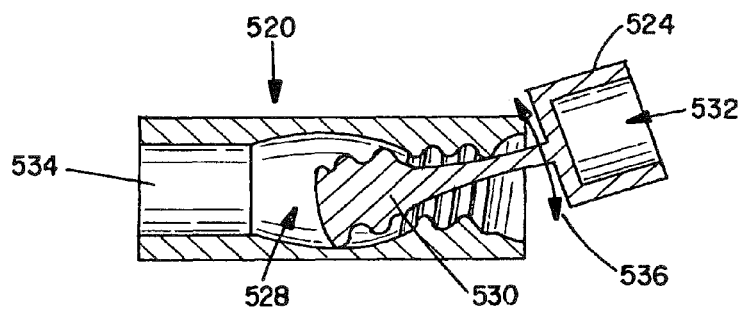
Figure 36:
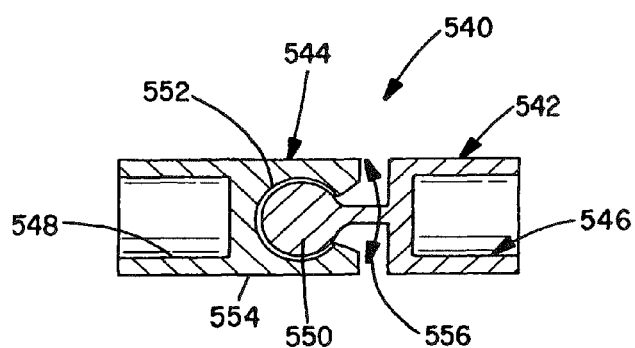
Figure 37A:
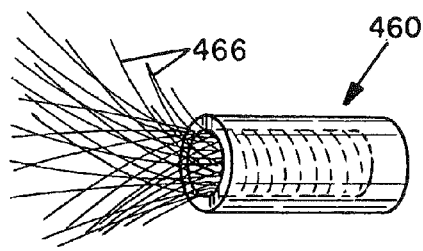
FIGS. 37A-B are side and end views respectively showing a clamping or securement connector device securing ends of a metal fabric.
Figure 37B:
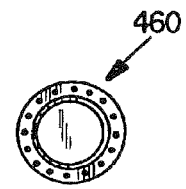

For example, FIGS. 35A-B and 36 illustrate two alternative connectors that may be used to prevent the fabric wire ends from unraveling and also to connect components together in an articulated manner. In FIG. 35B, the assembled clamp connector 520 is shown with a male threaded connector 524 threaded through threads 526 of the female connector 522 into cavity 528 such that the threads 530 of male connector 524 are no longer engaged. This permits male connector 524 to pivot about in connector 522. Cavities or recesses 532 and 534 are provided for retaining braided wire ends by crimp, weld, adhesive or other means. Components as shown in FIGS. 27A-H may, for example, be fabricated using a female wire end securement connector as at 522 on each end and the components shown in FIGS. 28A-G and FIGS. 29-34B may employ the male wire end retaining connector as at 524. The components may then be connected by threading action to one another. By threading the components through and beyond the internal threads 526 as shown in FIG. 35B, the assembly allows articulation between the members as shown by the arrow at 536. If this is not desired, the threads of each component may be allowed to remain engaged using fewer assemble turns between components.

FIG. 36 shows a cross-sectional view of a ball and socket end wire retaining connector 540 including a ball end component 542 and a socket end component 544 with wire end connection cavities 546 and 548, respectively, which may be similar to cavities 532 and 534. Assembly of the clamp connector device of FIG. 36 is achieved by compressing the ball 550 of ball end component 542 into the socket 552 of socket component 544 until they snap together. The socket 552 is provided with longitudinal slots (not shown) through the cylindrical wall 554 which allows it to deform sufficiently. The holding force between the assembled ball and socket connector 540 must be greater than the load experienced during implantation to ensure that the assembly remains intact. The ball and socket allows the assembled components to articulate as needed in any direction to align to anatomical conditions as indicated by arrow 556.

As indicated, the thread adapters of FIG. 39A-C are male to female (39A), male to male (39B) and female to female (39C). These adapters allow assembly of some components that otherwise may not be inter-connectable because of male/female thread mismatches and provide flexibility in creating a device shape and size.

It should be noted that, while the components to the device as shown in FIGS. 27A-34B are all shown fabricated of braided fabric, this is for illustration purposes only. Non-braided components are anticipated as well. For example, elastic middle components may be fabricated from springs including metal springs and non-metal elastic, resilient materials. The springs may be either tension or compression devices depending on the application, but generally will be tension springs seeking to pull the flange members toward each other as this is desirable for most applications. Polymers such as polyurethane or silicone or other polymers may also be used. The non-braided components similarly can be provided with compatible threaded end connectors, but the connectors may be fabricated differently from those for braided components. Individual components can incorporate polymeric strands as well as metal strands braided together or otherwise connected as by suture to one another.

It is anticipated that, in addition to the shapes shown in the drawing FIGS. 27A-33B, an array of sizes for each shape could be offered as well as additional shapes not shown for new applications or different anatomical conditions. In addition, it is anticipated that a device may be fabricated using multiple middle components to extend length without an end flange or disk. Multiple components such as that of FIG. 33A assembled together may form a flow restrictor or a shunt. Multiple components such as shown in FIG. 28A may form a long vessel occluder. In such a case, the diameter of the component would generally be sized larger than the vessel by approximately 10-30% to enable the vessel to retain the device in place.

Figure 27A:
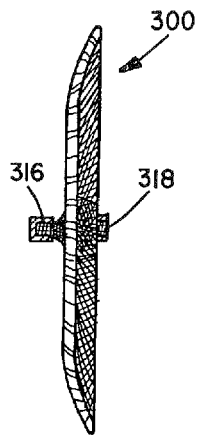
FIGS. 27A-I illustrate a plurality of examples of various disk shaped discrete components in accordance with the invention.
Figure 27B:
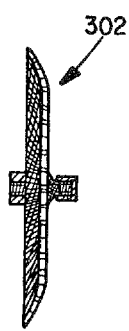
Figure 27C:
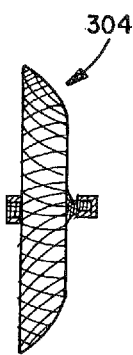
Figure 27D:
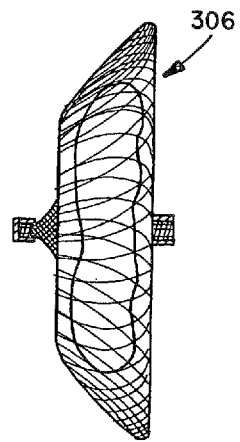
Figure 27E:
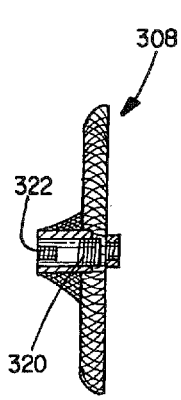
Figure 27F:
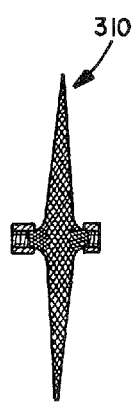
Figure 27G:
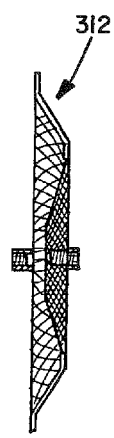
Figure 27H:
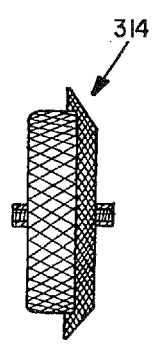
Figure 27I:
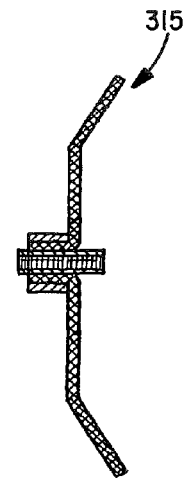
Figure 28A:
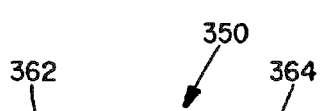
FIGS. 28A-G illustrate a plurality of examples of spacer and other discrete components in accordance with the invention.
Figure 28B:
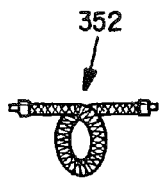
Figure 28C:
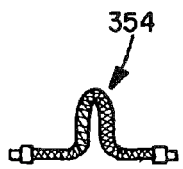
Figure 28D:
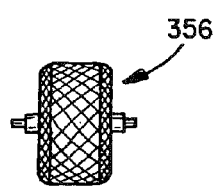
Figure 28E:
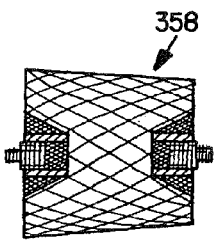
Figure 28F:
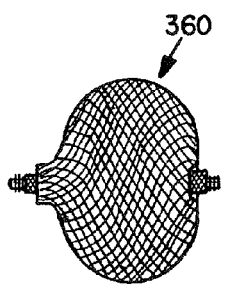
Figure 28G:
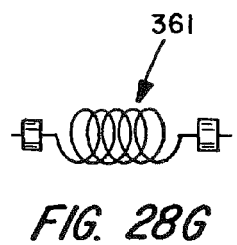
Figure 29:
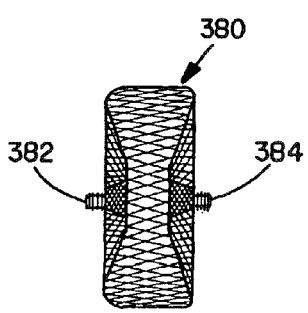

In other configurations, components as at 310 in FIG. 27F and 360 in FIG. 28F may be assembled to fabricate a device as is shown in FIG. 25 for use in occluding an aneurysm. Combining component 390 in FIG. 30 and 354 in FIG. 27C results in a device similar to that shown in FIGS. 15 and 21 for occluding a PDA. As indicated, FIG. 21 illustrates a multi-layer fabric device and FIG. 15 a single layer fabric device. All the components shown in FIGS. 27A-34B may be fabricated with one layer or multiple layers whereby any layer may be made of metal or polymer strands or a combination thereof. As additional component offerings, the braid wire diameter, pick and pitch may be altered as well for differing properties to affect stiffness, conformability, deliverability, collapsed profile or rate of, thrombosis.

Those skilled in the art will appreciate that in order to speed up the occlusion of a vessel, for example, the device may be coated with a suitable thrombogenic agent, filled with a polyester fiber layer or braided with an increased number of wire strands. Devices have been made preferably using a polyester fiber layer placed within the braided device and sutured in place. This layer may be a braided, knit or woven separate polyester filament. In this embodiment, the polymer layer is placed within or possibly overlaying the metal braided structure and sutured to the metal structure. If the polymer fabric is braided using a similar pitch and pick count for both the metal braid and polymer braid, the device can easily collapse and self expand as a unitary device for delivery using a catheter. A device using a fiber layer is also the preferred embodiment for an occlusion device, although use of multiple-layers of braided wire fabric may function in a similar manner to the polyester fabric combination to speed thrombosis. The interwoven fiber by its attachment to a clot retains the clot firmly within the device as it forms an occlusion.

The tubular braid used to fabricate occlusion devices, for example, using this invention may range from wire having a diameter of 0.002 to 0.005 inch, preferable in the range of 0.003 to 0.0035 inch and for a PDA device preferably 0.003 inch diameter. The number of wires in the tubular braid may vary from 36 to 144 but preferably is in the range of 72 to 144 and for a PDA device is preferably 144 wires. The pick count of the braid may vary from about 30 to about 100 and preferably from about 50 to about 80 and for a PDA device is most preferably about 70.

It is of an additional benefit to the assembly of multiple components if that the connectors of the assembled devices are of a small diameter and positioned at the axis of the device so that the flange or disk components can easily flex about the connectors and adjacent components to improve the conformability of the device to variable anatomical conditions.

In accordance with the use of the invention herein, the physician first assesses the anatomical situation of a patient in the catheter lab to determine the size and configuration of a device that would be best for the patient. The physician may then select individual components pre-steriled and stored in tyvek pouches, or the like, to be assembled in the catheter lab. A separately available device delivery system and delivery catheter may be selected as well. Delivery devices or elements (not shown) are well known and can take any suitable shape, preferably comprising an elongated flexible metal shaft or cable similar to a conventional guidewire or may be a hollow shaft, either configuration having a distal threaded connector. The individual device components are assembled in the sterile field by threading them together somewhat tightly. The delivery device may be placed through the delivery catheter such that the distal threaded end extends beyond the end of the delivery catheter. The proximal end of the assembled intravascular medical device is then threaded loosely onto the delivery system. In this manner, the delivery element may be back-loaded into the delivery catheter prior to placement of the delivery catheter into the body by proximal movement of the delivery device relative to the delivery catheter. When the medical device is withdrawn into the catheter, it is stretched axially, which allows the medical device profile to be reduced and the medical device pulled into the catheter. The catheter, delivery element and delivery system are now in a configuration for delivery into the body by normal catheter introduction techniques.

Alternatively, the delivery device may be back drawn into the distal end of a tear-away tapered introducer sleeve to reduce its diameter and then forward loaded into the proximal end of the delivery catheter. This procedure is preferred if the delivery catheter has already been introduced into the body of the patient.

A delivery device can also be used to urge the assembled medical device through the lumen of a catheter, or alternatively, through a long introducer sheath for deployment in a channel of the patient's body. When the assembled medical device is deployed out of the distal end of the catheter adjacent the treatment site, the assembled medical device is still attached to and retained by the delivery device. Once the proper position of the assembled device in the vessel or other location is confirmed, the shaft of the delivery device can be rotated about its axis to unscrew the connected clamp connector from the delivery device. Of course, the threaded connection may be at either end of the device depending on the anatomical situation and the desired or available means of access to the treatment site.

The torque used to assemble and retain the device components to each other must be higher than the unthreading torque required to separate the delivery system from the assembled device. This is usually accomplished by a stop in the delivery system threads designed to control the maximum torque applied.

By keeping the medical device attached to the delivery system until proper placement and size are confirmed, the operator can still retract the medical device for repositioning if it is determined that the medical device is not properly positioned in the first attempt or that the size of one or more components needs to be adjusted. This threaded attachment technique also allows the operator to control the manner in which the device is deployed out of the distal end of the catheter. When the medical device exits the catheter, it will tend to resiliently return to a preferred expanded shape which is set when the fabric is heat treated. When the medical device springs back into this shape, it may tend to act against the distal end of the delivery catheter, effectively urging itself forward beyond the end of the catheter. This spring action could conceivably result in improper positioning of the device. Since the threaded clamp connector or other securement device enables the operator to maintain control of the device during deployment, the shape-restoring spring action of the medical device can also be controlled and the operator can maintain control over the deployment to ensure proper positioning. A therapeutic medical device in accordance with the invention may be delivered and properly placed using two dimensional echocardiography and Doppler color flow mapping.

Generally, then in accordance with the present invention, there is provided further methods of treating physiological conditions of patients. In accordance with this method, a medical device suitable for treating a condition of interest, (occlusion, filter, shunt or flow restriction) which may be substantially in accordance with one of the embodiments outlined herein, is selected. For example, if a Patent Ductus Arteriosus (PDA) is to be treated, a PDA occlusion device similar to that of FIG. 15 or 21 can be assembled together and onto a delivery device. Once the appropriate medical device is assembled for delivery, a catheter may be positioned within a channel in the patient's body to place the distal end of the catheter adjacent the desired treatment site, such as immediately adjacent (or even within) the passageway or channel of the PDA. After proper placement of the PDA occlusion device, it may be detached and the delivery device and associated catheter withdrawn.

While a preferred embodiment of the present invention has been described, it should be understood that various changes, adaptations and modifications may be made therein without departing from the spirit of the invention and the scope of the appended claims.

What is claimed is:

1. A collapsible medical device comprising a longitudinal assembly of at least two selected discrete interconnectable components, configured for manual assembly and disassembly, at least one component comprising at least one layer of a plurality of metal strands woven into a tubular woven metal fabric having a proximal end and a distal end, at least one end having a securement device for securing at least one end attached to said tubular woven metal fabric, thereby gathering said strands and inhibiting unraveling of the strands, said tubular woven metal fabric having an expanded preset configuration shaped as a component of a device selected from the group consisting of occlusion devices, filters, shunts and flow restrictors, said expanded preset configuration being deformable to a lesser cross-sectional dimension for delivery through a channel in a patient's body, the woven metal fabric having a memory property whereby the collapsible medical device tends to return to said expanded preset configuration when unconstrained, wherein each interconnectable component includes a connector at each end of the respective interconnectable component configured to couple another connector or a delivery system to each respective end of the respective component, and wherein each connector of an interconnectable component on both ends of the component has the same configuration.

2. A medical device as recited in claim 1 wherein each said connector of each respective interconnectable component includes a securement device for securing an end of a tubular woven metal fabric.

3. A medical device as recited in claim 2 wherein the connectors of each respective interconnectable component are threaded.

4. A medical device as recited in claim 2 wherein the connectors of each respective interconnectable component are selected from the group consisting of male and female threads.

5. A medical device as recited in claim 2 wherein at least one of the securement devices comprises an inner sleeve and an outer tubular sleeve which clamp a plurality of fabric end strands of the tubular woven metal fabric therebetween and wherein said inner sleeve is threaded.

6. A medical device as recited in claim 1 wherein said selected discrete interconnectable components are interchangeable with other selected discrete interconnectable components to create medical devices with selected combinations.

7. A medical device as recited in claim 6 wherein the connectors of each respective interconnectable component are threaded.

8. A medical device as recited in claim 1 wherein the connectors of each respective interconnectable component are threaded.

9. A medical device as recited in claim 1, including an occluding polymer fiber layer retained within an expandable hollow central portion formed by said tubular woven fabric.

10. A medical device as recited in claim 9 wherein said polymer fiber is a polyester.

11. A medical device as recited in claim 1, wherein the metal fabric is manufactured from an alloy selected from the group consisting of stainless steel, nickel-titanium, and cobalt-chromium-nickel.

12. A medical device as recited in claim 1 wherein at least one of the at least two discrete inter-connectable components comprises more than one discrete layer of metal fabric extending between the connectors at each end.

13. A medical device as recited in claim 1 wherein the at least one component comprises a plurality of metal strands woven into a tubular woven metal fabric that has an expanded preset configuration in a shape selected from the group consisting of a disk or flange shape, bell, dumbbell, cylinder, tapered cylinder and cone.

14. A collapsible medical device as recited in claim 1 further comprising a longitudinal assembly of at least three selected discrete inter-connectable components and wherein said device includes a component having an expanded preset configuration shaped to create an occlusion of an abnormal opening in a body organ.

15. A medical device as recited in claim 14 wherein the at least three selected discrete interconnectable components comprise a pair of discrete interconnectable components and a middle spacer component connected to the connector of each interconnectable component such that the middle spacer component is disposed between the pair of interconnectable components.

16. A medical device as recited in claim 15 wherein the middle spacer component comprises a plurality of metal strands woven into a tubular woven metal fabric having a proximal end and a distal end, each end having a means for securing each end attached to said tubular woven metal fabric, said fabric having an expanded preset configuration deformable to a lesser cross-sectional dimension for delivery through a channel in a patient's body, the woven metal fabric having a memory property whereby the medical device tends to return to said expanded preset configuration when unconstrained.

17. A medical device as recited in claim 1 wherein said woven metal fabric further comprises an amount of polymer fibers.

18. A medical device as recited in claim 1 wherein at least one of the interconnectable components has an end connector for connection to a delivery system such that both of the interconnectable components of the longitudinal assembly are configured to be delivered and retracted together via attachment.

19. A collapsible medical device comprising a longitudinal assembly of at least two selected discrete interconnectable components, configured for manual assembly, and at least one component comprising at least one layer of a plurality of metal strands woven into a tubular woven metal fabric having a proximal end and a distal end, at least one end having a securement device for securing at least one end attached to said tubular woven metal fabric, thereby gathering said strands and inhibiting unraveling of the strands, said tubular woven metal fabric having an expanded preset configuration shaped as a component of a device selected from the group consisting of occlusion devices, filters, shunts and flow restrictors, said expanded preset configuration being deformable to a lesser cross-sectional dimension for delivery through a channel in a patient's body, the woven metal fabric having a memory property whereby the collapsible medical device tends to return to said expanded preset configuration when unconstrained, wherein each interconnectable component includes a connector at each end of the respective interconnectable component configured to couple another connector or a delivery system to each respective end of the respective component, and wherein each connector of an interconnectable component on both ends of the component has the same configuration.

* * * * *